United States Patent [19]
Mouchawar et al.

[11] Patent Number: 5,480,412
[45] Date of Patent: Jan. 2, 1996

[54] SYSTEM AND METHOD FOR DERIVING HEMODYNAMIC SIGNALS FROM A CARDIAC WALL MOTION SENSOR

[75] Inventors: Gabriel Mouchawar, Newhall; Kelly H. McClure, Simi Valley; Sheldon B. Moberg, Kagel Canon, all of Calif.

[73] Assignee: Pacesetter, Inc., Sylmar, Calif.

[21] Appl. No.: 154,800

[22] Filed: Nov. 16, 1993

[51] Int. Cl.$^6$ ............................................. A61N 1/365
[52] U.S. Cl. .......................... 607/6; 607/9; 607/24; 607/116
[58] Field of Search ............... 607/5–6, 9, 17–18, 607/24–26, 115–116; 128/668, 691

[56] References Cited

U.S. PATENT DOCUMENTS

| | | | |
|---|---|---|---|
| 3,815,611 | 6/1974 | Denniston, III | 607/17 X |
| 4,140,132 | 2/1979 | Dahl. | |
| 4,428,378 | 1/1984 | Anderson et al. | |
| 4,708,143 | 11/1987 | Schroeppel. | |
| 4,774,950 | 10/1988 | Cohen. | |
| 4,802,481 | 2/1989 | Schroeppel | 607/24 |
| 4,967,748 | 11/1990 | Cohen. | |
| 5,014,700 | 5/1991 | Alt. | |
| 5,031,615 | 7/1991 | Alt. | |
| 5,040,534 | 8/1991 | Mann et al. | |
| 5,040,535 | 8/1991 | Mann et al. | |
| 5,044,366 | 9/1991 | Alt. | |
| 5,156,148 | 10/1992 | Cohen | 607/17 X |

FOREIGN PATENT DOCUMENTS

052162A1   7/1993   European Pat. Off.

OTHER PUBLICATIONS

Bacharach, David W. et al., "Activity–Based Pacing: Comparison of a Device Using an Accelerometer Versus a Piezoelectric Crystal," *PACE*, vol. 15, pp. 188–196 (Feb. 1992).

Ovsyshcher, Ilya et al., "First Derivative of Right Ventricular Pressure, dP/dt, as a Sensor for a Rate Adaptive VVI Pacemaker: Initial Experience," *PACE*, vol. 15, pp. 211–218 (Feb. 1992).

Salerno, David M. et al., "Seismocardiography: A New Technique for Recording Cardiac Vibrations. Concept, Method, and Initial Observations," *Journal of Cardiovascular Technology*, vol. 9, No. 2, 1990, pp. 111–118.

Salerno, David M. M.D., Ph.D et al., "Seismocardiography for Monitoring Changes in Left Ventricular Function during Ischemia," *Chest*/100/4/Oct. 1991.

Salerno, David M. M.D., Ph.D et al., "Seismocardiographic Changes Associated with Obstruction of Coronary Blood Flow During Balloon Angioplasty," *The American Journal of Cardiology*, vol. 68, pp. 201–207 (Jul. 15, 1991).

Sandler, H. et al., "Miniature Implantable Accelerometers," pp. 165–174.

Piezo Electric Products, Inc., "Piezoceramic Design Notes," *Sensors* (6 pages) (Mar. 1984).

*Primary Examiner*—Angela D. Sykes
*Attorney, Agent, or Firm*—Lisa P. Weinerg; Harold C. Schloss

[57] ABSTRACT

A processing system and method are provided for deriving an improved hemodynamic indicator from cardiac wall acceleration signals. The cardiac wall acceleration signals are provided by a cardiac wall motion sensor that responds to cardiac mechanical activity. The cardiac wall acceleration signals are integrated over time to derive cardiac wall velocity signals, which are further integrated over time to derive cardiac wall displacement signals. The cardiac wall displacement signals correlate to known hemodynamic indicators, and are shown to be strongly suggestive of hemodynamic performance. An implantable cardiac stimulating device which uses cardiac wall displacement signals to detect and discriminate cardiac arrhythmias is also provided.

26 Claims, 6 Drawing Sheets

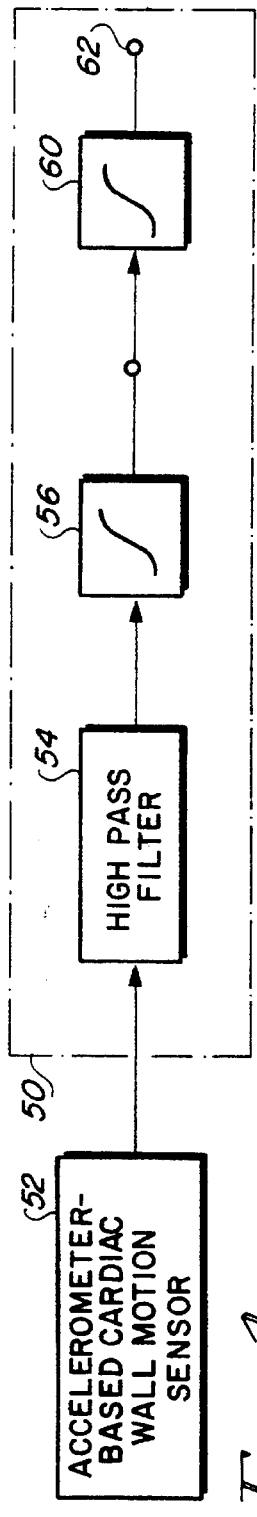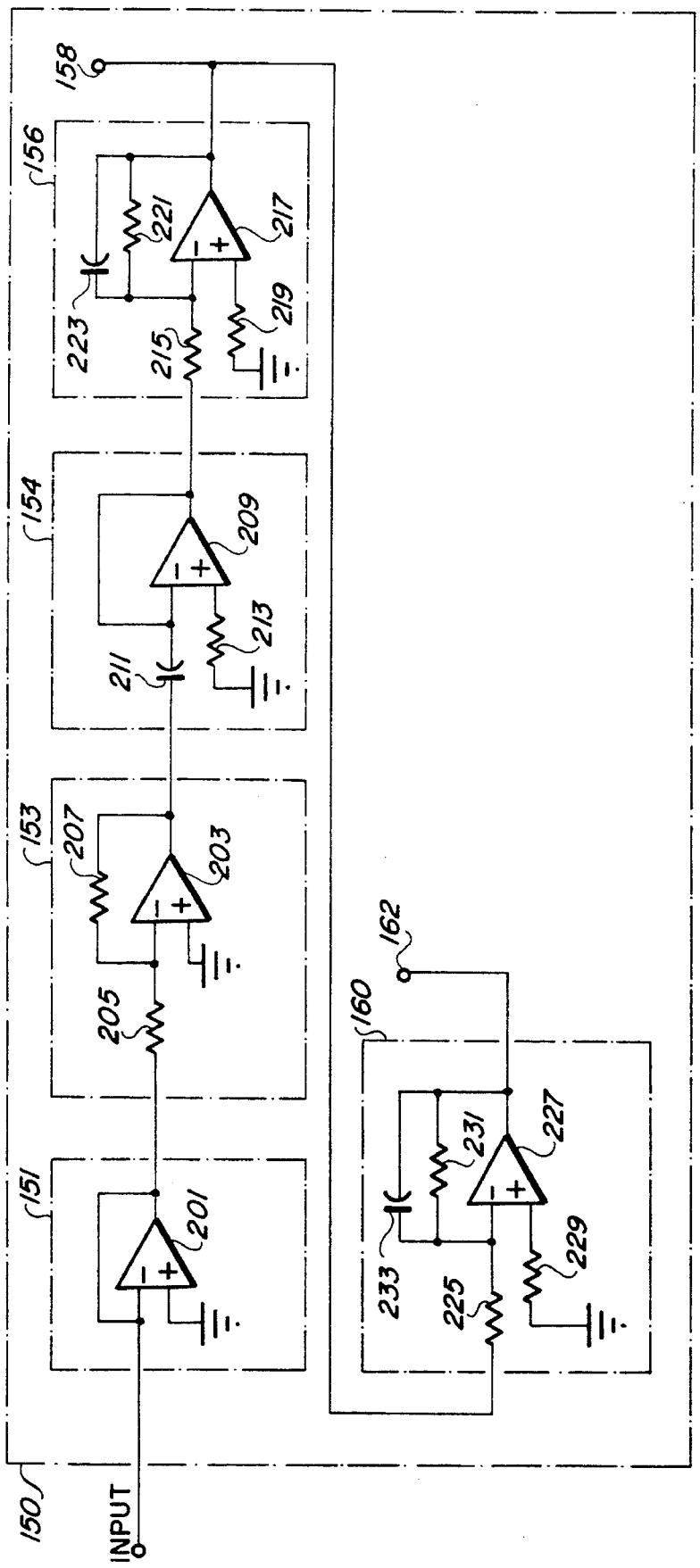

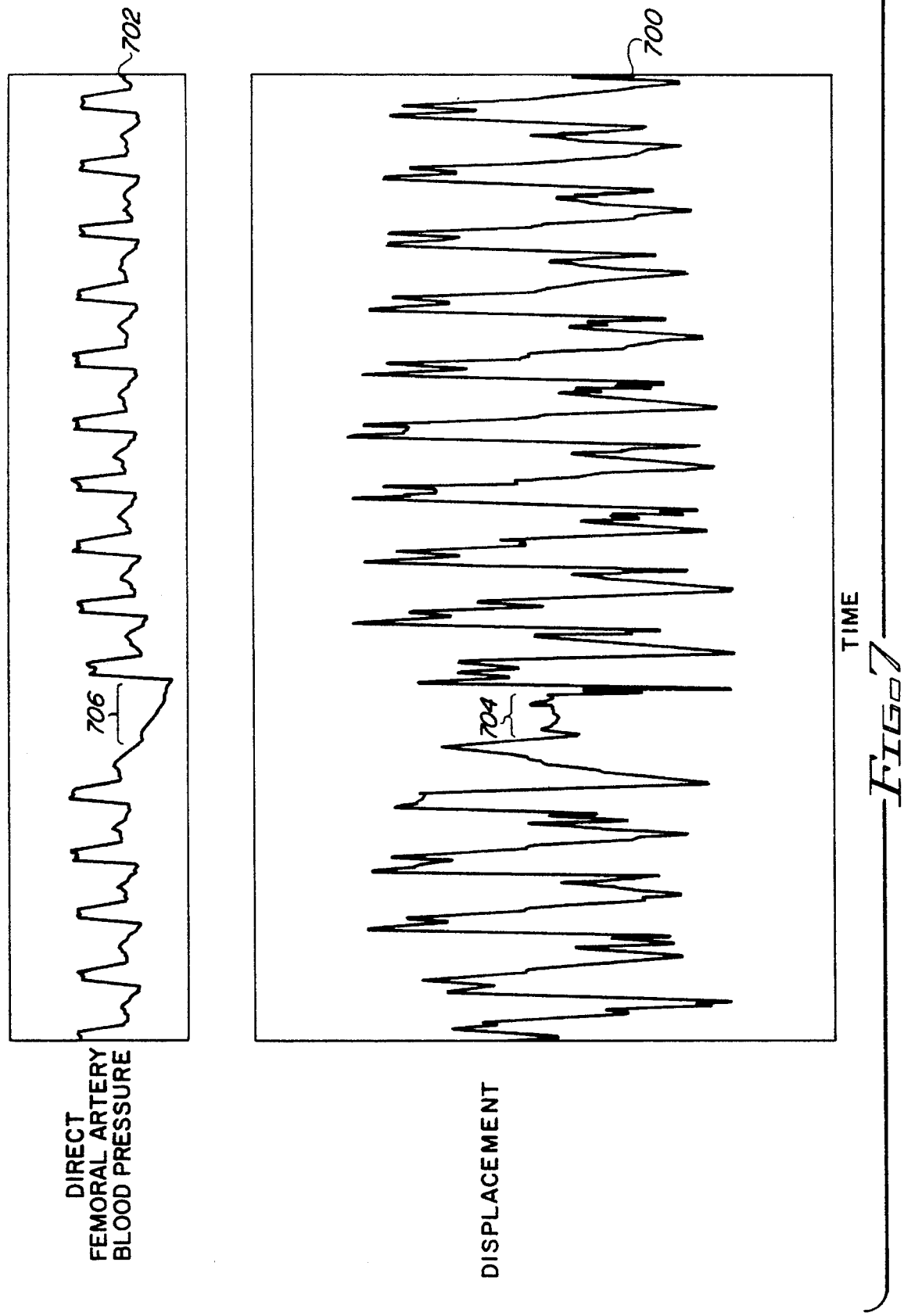

5,480,412

SYSTEM AND METHOD FOR DERIVING HEMODYNAMIC SIGNALS FROM A CARDIAC WALL MOTION SENSOR

FIELD OF THE INVENTION

This invention relates to implantable medical devices, including implantable pacemakers and implantable defibrillators, as well as implantable cardioverters and cardioverter/defibrillators. More particularly, this invention relates to a processing system and method for use with such devices, for deriving cardiac wall displacement from a cardiac wall motion sensor signal and for using cardiac wall displacement as a hemodynamic indicator.

BACKGROUND OF THE INVENTION

Implantable cardiac stimulating devices which provide therapeutic electrical stimulation in response to a variety of pathological cardiac arrhythmias are well known in the art. These devices may provide a single type of therapy (e.g., bradycardia pacing therapy) or they may be capable of providing "tiered therapy," in which the type of electrical stimulation administered is determined in accordance with the severity of the arrhythmia, with more aggressive therapies being applied in response to more severe arrhythmias.

Effective delivery of therapy from an implantable cardiac stimulating device depends upon accurate measurement of intrinsic cardiac activity. Devices that provide tiered therapy must not only be capable of detecting the onset of an arrhythmia, but must also be capable of discerning particular types of arrhythmias in order to deliver an appropriate form of electrical stimulation therapy. For example, if a hemodynamically unstable ventricular tachycardia is incorrectly diagnosed as a relatively less severe arrhythmia, valuable time may be lost if an inappropriate, less aggressive therapy, such as antitachycardia pacing, is applied. On the other hand, if a high rate, hemodynamically stable tachycardia is incorrectly diagnosed as ventricular fibrillation, the patient may consciously experience a painful high energy defibrillation shock.

Measurement of intrinsic cardiac activity is also important for devices that provide bradycardia pacing therapy. For instance, a demand pacemaker can inhibit delivery of a pacing pulse when a naturally occurring heartbeat is sensed within a predetermined period of time following a preceding heart beat (the time period commonly referred to as the "escape interval"). Pacing pulse inhibition is desirable because it extends battery life. To achieve this desirable result, the device must be capable of monitoring intrinsic cardiac activity.

Many implantable cardiac stimulating devices detect cardiac arrhythmias by monitoring cardiac electrical activity—i.e., the intracardiac electrogram (IEGM). The IEGM is typically sensed by electrodes that are also used to deliver electrical stimulation to the cardiac tissue. However, under many circumstances, it is difficult to sense the IEGM. For example, the device may not be able to discern the IEGM over external interference. As a result, an implantable cardiac stimulating device may have difficulty detecting the onset of an arrhythmia. As another illustration, implantable cardiac stimulating devices that provide bradycardia pacing therapy may be inhibited from sensing cardiac electrical activity during a period of time immediately following the delivery of a pacing pulse, due to the presence of a pulse-induced after-potential in the vicinity of the pacing electrodes.

Unfortunately, IEGMs are only the electrical trigger signal that proceeds the mechanical activity of the cardiac muscle. While, IEGMs are useful in most cases in determining the rate of contraction of the cardiac muscle, they do not carry information regarding the mechanical vigor of the resulting contraction. To properly assess the performance of the heart as a functioning pump, two pieces of information are needed: the rate of pumping and the amount of fluid displaced. Only rate information is available when a cardiac device monitors the IEGMs. What is needed then, is a sensor which can monitor both rate and the amount of fluid displaced.

Some implantable cardiac stimulating devices monitor physiologic parameters, other than the IEGM, which reflect hemodynamic performance. For example, U.S. Pat. No. 4,774,950 to Cohen refers to a system that detects cardiac arrhythmias by measuring mean pressure at a variety of locations (e.g., mean arterial pressure, mean right ventricular pressure, mean left atrial pressure, mean left ventricular pressure or mean central venous pressure). For a selected mean pressure, a short term current mean pressure is compared to a long term mean baseline pressure, and if they differ by a predetermined value, the patient may be deemed to be experiencing a cardiac arrhythmia. The mean pressure data may also be used in combination with heart rate measurements to detect arrhythmias.

The use of another hemodynamic indicator, blood oxygen level, is described in U.S. Pat. No. 4,967,748 to Cohen. Blood oxygen level is measured at a particular site in the circulatory system of a patient. A comparison is made between a short term sensed blood oxygen level and a baseline blood oxygen level, and if they differ, the patient may be deemed to be experiencing a cardiac arrhythmia.

Unfortunately, the use of hemodynamic indicators such as mean pressure and blood oxygen level may have certain associated drawbacks. One drawback is that certain hemodynamic indicators may not respond rapidly to the onset of an arrhythmia. Thus, an implantable cardiac stimulating device that relies on certain hemodynamic signals to detect cardiac arrhythmias may not deliver therapy as rapidly as desired. Another drawback is that the measurement of certain hemodynamic indicators requires the use of sensors that must be delivered to sites that do not normally receive electrical stimulation. Thus, additional leads may be required, which undesirably add cost to the implantable system and complexity to the surgical procedure during which the leads are implanted.

One proposed solution which overcomes some of the drawbacks associated with the use of the IEGM and certain hemodynamic indicators is described in commonly assigned, copending U.S. patent application Ser. No. 08/091,636, filed 7/14/93, of Causey and Moberg, entitled "Implantable Leads Incorporating Cardiac Wall Motion Sensors and Method of Fabrication and a System and Method for Detecting Cardiac Arrhythmias Using a Cardiac Wall Motion Sensor Signal," which is hereby incorporated by reference in its entirety. That patent application describes implantable leads which incorporate cardiac wall motion sensors that provide signals indicative of cardiac mechanical activity. More particularly, the signals are representative of cardiac wall accelerations as experienced by the motion sensors.

The cardiac wall motion sensors of the above-incorporated patent application rapidly respond to the onset of arrhythmias. The signals are not subject to electrical interference from pacemakers induced after-potentials and external sources. The raw acceleration signals advantageously provide an accurate and reliable indication of cardiac mechanical activity. However, it would be even more desirable to be able to process the raw signals provided by the cardiac wall motion sensors in order to derive signals that strongly correlate to the hemodynamic performance of a patient's heart. It would also be desirable to provide an implantable cardiac stimulating device that uses the derived hemodynamic signals to determine when (and what form of) therapeutic electrical stimulation should be administered.

SUMMARY OF THE INVENTION

The disadvantages and limitations associated with the use of the IEGM and certain hemodynamic indicators for monitoring cardiac activity are overcome by the present invention. This invention is directed toward a processing system for receiving signals indicative of cardiac mechanical activity from cardiac wall motion sensors, and for using the sensor signals to derive an improved hemodynamic indicator. More particularly, the processing system of the present invention receives signals from a cardiac wall motion sensor that is responsive to cardiac wall accelerations. The processing system processes the cardiac wall motion sensor signals to derive signals representative of cardiac wall velocity and cardiac wall displacement.

Although the cardiac wall accelerations and velocity signals may themselves be useful, the primary purpose of the processing system is to derive signals representative of cardiac wall displacement which, as described below, are strongly suggestive of hemodynamic performance.

To better understand the advantages of using cardiac wall displacement as a hemodynamic indicator, a brief description of the impact of various cardiac arrhythmias on hemodynamic performance may be useful. A non-malignant heart pumps blood through the circulatory system by expanding and contracting in a rhythmic fashion at a physiologically acceptable rate. When a patient suffers from a cardiac arrhythmia, the heart expands and contracts in a noticeably different manner. For example, if the patient suffers from bradycardia, the patient's heart expands and contracts at a rate that is slower than normal. When a patient experiences a form of tachycardia, the heart expands and contracts more rapidly than normal; however, the heart may not expand and contract as vigorously, because the reduced time between beats provides the chambers of the heart with less of an opportunity to fill with blood. When a patient experiences an episode of fibrillation, the heart quivers chaotically as a result of asynchronous contractions of the heart cells, which prevents it from ejecting blood in a normal fashion.

Cardiac wall displacement provides information regarding both the rate at which the heart is pumping and the amount of fluid that is being displaced. Thus, the signals representative of cardiac wall displacement, as provided by the processing system of the present invention, are strongly suggestive of the hemodynamic performance of the patient's heart.

To illustrate, a cardiac wall displacement signal from a patient suffering from bradycardia exhibits excursions that appear at a slower rate than normal (i.e., the excursions would occur as the heart expands and contracts at the abnormally slow rate), but the amplitude of each excursion may be about normal or slightly larger than normal due to the increased filling time. This would indicate that the total volume of blood being pumped by the heart (also known as cardiac output) is abnormal (perhaps pathological), even though the volume of blood being pumped at each beat (also known as stroke volume) may be about normal or slightly higher than normal. Cardiac wall displacement signals from a patient experiencing a form of tachycardia (or fibrillation) would similarly exhibit excursions that track the expansion and contraction (or quivering) of the heart, and as in the bradycardia case, the signals would be indicative of hemodynamic compromise. Indeed, as is shown below, the cardiac wall displacement signals provided by the processing system of the present invention is a measure of stroke volume and strongly correlates to arterial blood pressure signals. Arterial blood pressure is a physiologic parameter that is known to be representative of hemodynamic performance.

In a preferred embodiment, the processing system of the present invention includes a high pass filter which receives signals from a cardiac wall motion sensor. The received signals are representative of accelerations of a region of the cardiac wall that the sensor is mechanically coupled to (e.g., the sensor may be mounted within the distal end of an implantable lead which is in contact the selected region of the cardiac wall). The raw cardiac wall motion sensor signals may be delivered to the processing system within an implantable cardiac stimulating device via conductors running the length Of the implantable lead, in which case the proximal end of the lead may have a connector that mates with a connector on the implantable cardiac stimulating device.

The high pass filter selects signals associated with cardiac wall motion and attenuates signals with frequencies lower than the cardiac cycle, such as those representative of body motion (including respiration). The processing system then integrates the filtered signals over time in order to derive signals representative of cardiac wall velocity. To derive signals representative of cardiac wall displacement, the processing system integrates the cardiac wall velocity signals over time. It may also be desirable for the processing system to further process the cardiac wall displacement signals in order to derive peak-to-peak displacement signals.

The precise manner by which cardiac wall displacement signals are derived from cardiac wall motion sensor signals may be varied without departing from the spirit of the invention. For example, discrete analog or digital components may be used to filter and integrate the cardiac wall motion sensor signals. Preferably, integrated circuitry on the implantable cardiac stimulating device hybrid is used to derive the cardiac wall displacement signals. Alternatively, the cardiac wall motion sensor signals may be processed (either partially or completely) by a microprocessor, which can perform the processing steps described above by executing appropriate program instructions.

In another aspect of the invention, a method of processing cardiac wall motion sensor signals to derive cardiac wall displacement signals is provided.

The cardiac wall displacement signals derived in accordance with the principles of the present invention may be used by an implantable cardiac stimulating device to detect and discriminate cardiac arrhythmias. As described above, cardiac wall displacement is strongly suggestive of hemodynamic performance. Thus, the cardiac wall displacement signals reflect the onset and the type of hemodynamically compromising cardiac arrhythmias (e.g., bradycardia, tachycardia or fibrillation) experienced by the patient. This information can be used by the implantable cardiac stimulating device to select an appropriate form of electrical stimulation therapy to administer to the patient (e.g., bradycardia pacing, antitachycardia pacing, cardioversion shocks or defibrillation shocks).

In yet another embodiment, the cardiac wall displacement signals may be used in an implantable monitoring device to monitor hemodynamic performance of the heart. For example, cardiac wall displacement signals can be used to detect premature ectopic beats. The number of ectopic beats per hour may be a useful indicator for patients undergoing serial drug testing for the suppression of such events.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 1 is a block diagram of a preferred embodiment of a processing system for deriving cardiac wall displacement in accordance with the principles of the present invention;

FIG. 2 is a schematic diagram of a preferred embodiment of the processing system of FIG. 1 which is implemented using analog circuitry in accordance with the principles of the present invention;

FIG. 7 is a graph showing a direct arterial blood pressure signal (the upper channel) as measured in the femoral artery and a cardiac wall displacement signal (the lower channel) derived in accordance with the principles of the present invention, both plotted simultaneously as a function of time, each indicative of a subject that experienced an ectopic heartbeat during normal sinus rhythm.

DETAILED DESCRIPTION OF THE PREFERRED EMBODIMENTS

Figure 3:
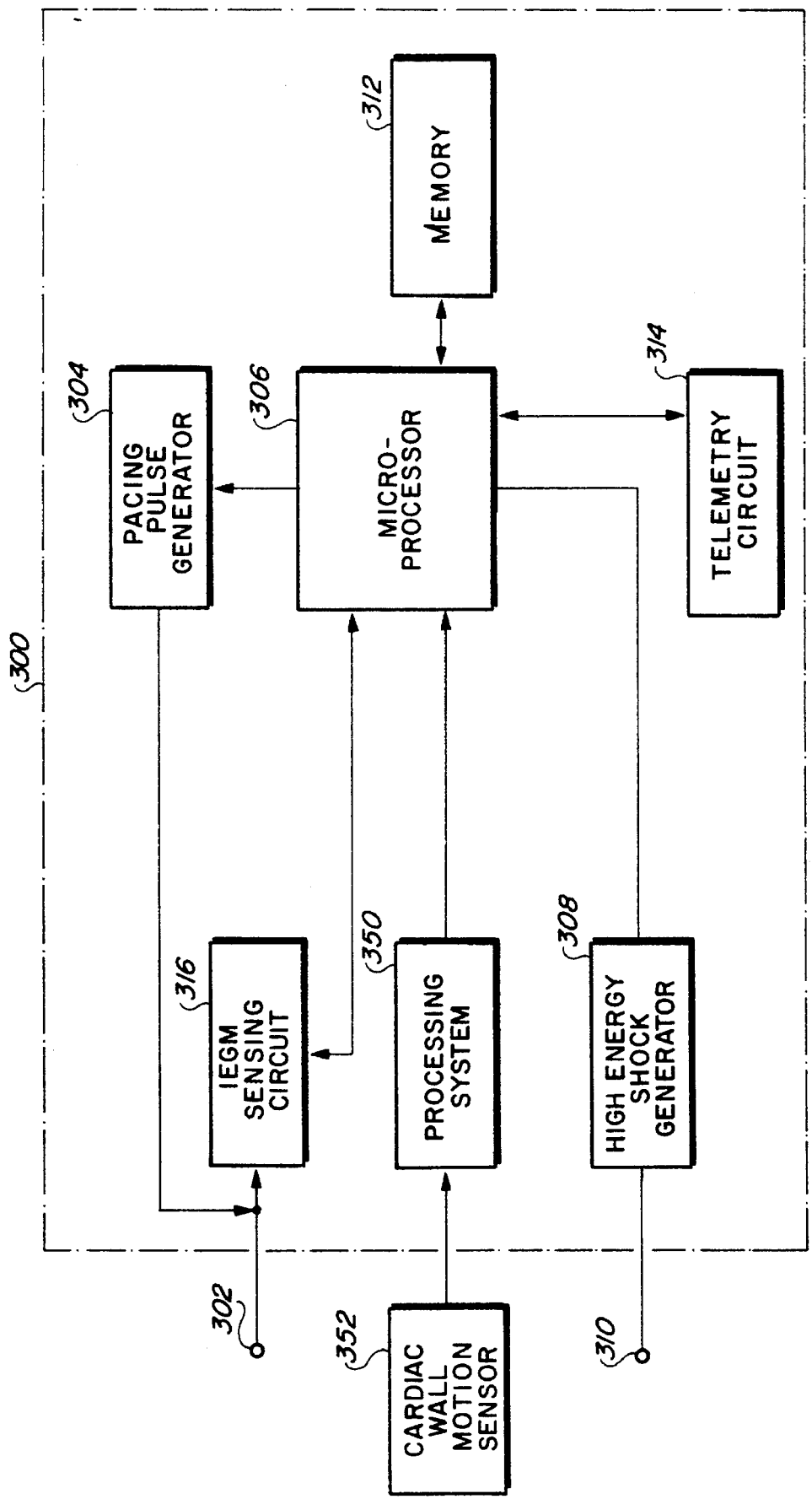
FIG. 3 is a block diagram of a preferred embodiment of an implantable cardiac stimulating device which uses cardiac wall displacement as a hemodynamic indicator to administer therapeutic electrical stimulation to cardiac tissue in accordance with the principles of the present invention.

In FIG. 1, a preferred embodiment of a processing system 50 for deriving an improved hemodynamic indicator in accordance with the principles of the present invention is described. The processing system 50 is intended to receive input signals from an accelerometer-based cardiac wall motion sensor 52. The cardiac wall motion sensor 52 is mechanically coupled to a region of a patient's cardiac wall (not shown) in a manner that allows the cardiac wall motion sensor 52 to respond to cardiac wall accelerations associated with cardiac contractile activity.

Sensors that are particularly well-suited for use as the cardiac wall motion sensor 52 are disclosed in the above-incorporated U.S. patent application Ser. No. 08/091,636. That patent application discloses several types of implantable leads, including endocardial leads, myocardial active-fixation leads and epicardial patch electrodes, all of which may incorporate accelerometer-based cardiac wall motion sensors. These leads are not only useful for mechanically coupling the cardiac wall motion sensor 52 to the cardiac wall—they may also provide the electrodes (not shown) which are used to administer therapeutic electrical stimulation to cardiac tissue and to detect IEGMs, thereby reducing the number of leads that need to be implanted in the patient's body.

The processing system 50 includes a high pass filter 54, which receives raw acceleration signals from the cardiac wall motion sensor 52. The high pass filter 54 selects signals associated with cardiac wall motion, and attenuates unwanted signals, such as those associated with body motion (in a manner described in greater detail below). The filtered acceleration signals are received by a first integrator circuit 56, which integrates the filtered acceleration signals over time to derive cardiac wall velocity signals.

As mentioned above, although the primary purpose of the present invention is to use cardiac wall displacement as a hemodynamic indicator, the cardiac wall velocity signals may be independently useful. For example, velocity signals may be used as an indicator of cardiac contractility or sympathetic drive (i.e., an adrenaline-induced increase in heart action). Furthermore, since velocity is the rate of change of displacement, it also provides a signal correlating to inflow and outflow of blood. The velocity signals are made available at a node 58, should this information be deemed valuable in connection with diagnosis or treatment for a particular patient.

The velocity signals derived by the first integrator circuit 56 are received by a second integrator circuit 60, which integrates the velocity signals over time to derive cardiac wall displacement signals, which are made available at a node 62. Although it may be possible to make beneficial use of the cardiac wall displacement signals available at the node 62, it is preferable to further process the signals to derive the peak-to-peak displacement signals.

Analog peak-to-peak detectors are well known in the art. However, in the preferred embodiment, peak-to-peak detection is achieved by a microprocessor 70. The cardiac wall displacement signals available at the node 62 are directed to an analog-to-digital (A/D) converter 66 via a multiplexer circuit 64. The digitized signal at the output 68 of the A/D converter 66 is then received by the microprocessor 70. A control program stored in a memory 72 enables the microprocessor 70 to determine a variety of information about the cardiac displacement signal, including (but not limited to) peak-to-peak information.

Examples of other analog signals that are also known in the art to be multiplexed to the A/D converter 66 for processing by the microprocessor 70 include: atrial and ventricular IEGMs, battery voltage, battery current and/or battery impedance. If desired, the output of the accelerometer-based cardiac wall motion sensor 52, either before or after being processed through the high pass filter 54, could be directed to the microprocessor 70. Similarly, the velocity signals available at the node 58, could be directed to the microprocessor 70.

The precise manner by which the processing system 50 is implemented may be varied without departing from the spirit of the invention. For example, the high pass filter 54, the first and second integrator circuits 56 and 60 may be implemented using discrete analog components (see FIG. 2 below) or digital components, or some combination of the two. Preferably, the processing system 50 is implemented using integrated circuitry on a hybrid (not shown) of an implantable cardiac stimulating device (described below in connection with FIG. 3). In an alternative embodiment of the invention, several or all of the processing steps described above may be accomplished by a microprocessor (shown in FIG. 3) in the implantable cardiac stimulating device. For a microprocessor-based embodiment, the block diagram of FIG. 1 represents a sequence of processing steps which may be performed by the microprocessor.

A preferred embodiment of the processing system 50 (FIG. 1) which is implemented using analog circuitry that may be conveniently integrated into hybridized circuitry of an implantable cardiac stimulating device is shown in FIG. 2. For ease in comparing the components shown in FIG. 2 to the block diagram of FIG. 1, like components are numbered using essentially the same reference numerals, except that they are increased by 100 in FIG. 2.

A processing system 150 includes a buffer 151 which receives the raw acceleration signals from the cardiac wall motion sensor 52 (FIG. 1). The buffer 151 is used for impedance matching to downstream circuitry without introducing any phase shift. The buffer 151 may be implemented using a conventional operational amplifier 201 which has its inverting input coupled to its output.

The buffer 151 may be coupled to an amplifier 153 to increase the strength of the input signals. The amplifier 153 may comprise an operational amplifier 203, a first bias resistor 205 (coupled between the output of the operational amplifier 201 and the inverting input of the operational amplifier 203) and a second bias resistor 207 (coupled between the inverting input and the output of the operational amplifier 203). The bias resistors 205 and 207 (which may both have resistances of about 25 KΩ) are used to set the gain Of the amplifier 153. As is well known in the art, the gain of the amplifier 153 may be changed by altering the ratio of the second bias resistor 207 to the first bias resistor 205, for example, by changing the value of the first bias resistor to about 5 KΩ would change the gain (i.e., the ratio of the resistor 207 to the resistor 205) from about 1 to about 5.

The amplifier 153 is coupled to a high pass filter 154 which includes an operational amplifier 209, a capacitor 211 (coupled between the output of the operational amplifier 203 and the non-inverting input of the operational amplifier 209) and a resistor 213 (coupled between the non-inverting input of the operational amplifier 209 and ground) having a resistance of about 14 KΩ. Changing the value of the capacitor 211 will correspondingly change the frequency threshold of the high pass filter 154. To attenuate signals corresponding to body motion, the value of the capacitor 211 must be selected to filter signals in the range of about 0.1 Hz to about 2 Hz. Given that resistor 213 is 14 KΩ, the value of the capacitor 211 may be between about 47 µF and about 2 µF, respectively.

The high pass filter 154 is coupled to a first integrator circuit 156 which includes an operational amplifier 217, a first resistor 215 (coupled between the output of the high pass filter 154 and the inverting input of the operational amplifier 217), a second resistor 219 (coupled between the non-inverting input of the operational amplifier 217 and ground), a third resistor 221 (coupled between the output and the inverting input of the operational amplifier 217), and a capacitor 223 connected in parallel with the resistor 221. In the preferred embodiment, the resistor 215 has a resistance of about 2.5 KΩ, while the resistors 219 and 221 may be about 2.2 KΩ and 25 KΩ respectively. The capacitor 223 preferably has a capacitance of about 4.7 µF. In addition to integrating the input signal, the integrator 156 also amplifies the signal in proportion to the ratio of the resistor 221 to the resistor 215 (which set the gain of the amplifier). The output of the first integrator circuit 156 may be connected to an output terminal 158, in order to provide signals representative of cardiac wall velocity.

The second integrator circuit 160 (which is essentially identical to the first integrator circuit 156) includes an operational amplifier 227, three resistors 225, 229 and 231, and a capacitor 233. The resistors 225, 229 and 231, and the capacitor 233 have about the same values as, respectively, the resistors 215, 219 and 221, and the capacitor 223. The output of the second integrator circuit 160 may be coupled to an output terminal 162 to provide cardiac wall displacement signals. Each of the integrator circuits is biased so that a gain of 10 is applied to the input signal (because the integrator naturally reduces the high frequency component of the input signal). Therefore, the signal has a gain of 100 (i.e., a gain of 10 applied by the first integrator 156, times the gain of 10 applied by the second integrator 160). While the cardiac wall displacement signal at output terminal 162 may be used directly, it may be desirable to have some type of a detector circuitry, such as, a threshold detector, a comparator, a frequency counter, etc. In the preferred embodiment, as mentioned above, a peak-to-peak detector is used to provide information corresponding the strength or vigor or the contraction.

In FIG. 3, a block diagram is shown representing an implantable cardiac stimulating device 300 which provides therapeutic electrical stimulation to cardiac tissue in response to cardiac arrhythmias detected by using cardiac wall displacement as a hemodynamic indicator. The implantable cardiac stimulating device 300, as described below, is capable of providing bradycardia pacing therapy as well as higher energy therapies, such as cardioversion and defibrillation shocks. However, the principles of the present invention can be applied equally as well to simpler devices, such as dedicated bradycardia pacemakers, defibrillators or other implantable medical devices which may desire monitoring of hemodynamic performance, in view of the description below.

The implantable cardiac stimulating device 300 delivers therapeutic electrical stimulation to a patient's heart (not shown) through leads 302 and 310 which are attached at one end to the implantable cardiac stimulating device 300, and at the other end (not shown) to a selected region of cardiac tissue. In the embodiment shown in FIG. 3, at least one pacing lead 302 is used to deliver pacing pulses generated by a pacing pulse generator 304 (which may be conventional) in accordance with instructions provided by a microprocessor 306. The pacing pulse generator 304 may be used to generate pacing pulses in any of the modes known for treating bradycardia and in addition, may be used to generate pacing pulses in a sequence known for interrupting tachycardia.

The implantable cardiac stimulating device 300 also provides higher energy shock therapies to interrupt more severe cardiac arrhythmias. For example, cardioversion shocks may be administered to revert ventricular tachycardia (VT), and defibrillation shocks may be administered to interrupt ventricular fibrillation (VF). These high energy shocks are generated by a high energy shock generator 308 (which may be conventional) under the control of the microprocessor 306. The high energy shocks are delivered to the patient's heart through at least one shocking lead 310. Although the pacing lead 302 and the shocking lead 310 are shown as physically separate leads, their respective electrodes may be provided by a single lead (not shown). Indeed, a great variety of lead configurations may be used in accordance with the principles of the present invention, so as to not diminish the flexibility that a medical practitioner normally has when selecting leads that meet the needs of a particular patient.

The manner by which the implantable cardiac stimulating device 300 delivers pacing therapy and higher energy shock therapies is controlled by the microprocessor 306, to some extent, in accordance with parameters stored in a memory 312. Many of these parameters are known in the art (i.e., escape interval, refractory period, cardioversion shock energy, defibrillation shock energy, etc.), and they may be programmed by a medical practitioner using a programming unit (not shown) that communicates with the microprocessor 306 through a telemetry circuit 314.

However, static parameters stored in the memory 312 do not provide the microprocessor 306 with all of the information necessary to control the manner by which therapies are administered by the implantable cardiac stimulating device 300. Rather, it is necessary for the microprocessor 306 to receive information pertaining to the patient's current cardiac condition in order to detect the onset of an arrhythmia and to select an appropriate form of electrical stimulation therapy in response to a detected arrhythmia.

In the embodiment shown in FIG. 3, the microprocessor 306 receives information pertaining to the patient's cardiac condition from two sources—an IEGM sensing circuit 316 and a processing system 350 (such as the processing system 50 described above in connection with FIG. 1). The IEGM sensing circuit 316 (which may be conventional), receives the patient's IEGM during periods when pacing pulses are not being administered through the pacing lead 302. The IEGM sensing circuit 316 uses the patient's IEGM to provide the microprocessor 306 with information pertaining to the patient's cardiac rate. This information may be used by the microprocessor 306 to cause the implantable cardiac stimulating device 300 to respond to the onset of an arrhythmia with an appropriate form of electrical stimulation therapy from either the pacing pulse generator 304 or the high energy shock generator 308.

However, as explained above, the IEGM may become difficult to use at times, because it doesn't carry hemodynamic information and it may be subject to interference from, for example, after-potentials which appear in the vicinity of the pacing electrodes (not shown) of the pacing lead 302 for a period of time immediately following the delivery of pacing pulses. To overcome such difficulties, the implantable cardiac stimulating device 300 also includes a processing system 350, which provides cardiac wall displacement signals to the microprocessor 306. The cardiac wall displacement signals are derived from the raw acceleration signals provided by a cardiac wall motion sensor 352 (such as the cardiac wall motion sensor 52 described above in connection with FIG. 1). The cardiac wall displacement signals are a sensitive hemodynamic signal which is proportional to stroke volume and are not subject to interference from after-potentials, and unlike certain other hemodynamic indicators, they allow the microprocessor 306 to rapidly detect the onset of cardiac events which may be hemodynamically compromising.

The microprocessor 306 may be programmed by a medical practitioner via the telemetry circuit 314 to operate in one of several modes. For example, the microprocessor 306 may be programmed to respond to either the processing system 350 or to the IEGM sensing circuit 316 exclusively. Alternatively, the microprocessor 306 may be programmed to respond primarily to either the processing system 350 or to the IEGM sensing circuit 316, and to use, as a secondary source of information, the source not designated as the primary source. For instance, the IEGM sensing circuit 316 may be used to confirm the onset of an episode of ventricular fibrillation first detected using the cardiac wall displacement signals provided by the processing system 350. Further, the extent to which a particular source of information is used may be programmed independently for each type of electrical stimulation therapy. For example, the processing system 350 may be designated as the primary source of information for therapies provided by the high energy shock generator 308, whereas the IEGM sensing circuit may be the primary source of information for bradycardia pacing therapy provided by the pacing pulse generator 304.

In the embodiment shown in FIG. 3, the cardiac wall displacement signals are derived using circuitry in the processing system 350 (such as the circuitry described above in connection with FIG. 2). However, therapeutic electrical stimulation may be administered equally as well by an implantable cardiac stimulating device which, instead of the processing system 350, includes a microprocessor that is programmed to derive cardiac wall displacement from raw acceleration signals provided by the cardiac wall motion sensor 352.

The manner by which the implantable cardiac stimulating device 300 uses the cardiac wall displacement signals to administer electrical stimulation therapy may be fully appreciated by reference to a series of signals shown in FIGS. 4–7. In FIGS. 4–7, cardiac wall displacement signals 400, 500, 600 and 700 derived in accordance with the principles of the present invention are described and compared to direct femoral artery blood pressure signals 402, 502, 602 and 702, respectively. The arterial blood pressure signals 402, 502, 602, 702 were measured by cannulating femoral artery with a fluid filled catheter connected to a pressure transducer, as is well known in the art. The cardiac wall displacement signals 400, 500, 600 and 700 are also shown as a function of time and synchronized to the blood pressure signals 402, 502, 602 and 702, respectively. Although direct blood pressure is an excellent hemodynamic signal, its use is limited to the setting of an operating room. For purposes of present invention, the use of direct blood pressure as a reference signal serves to illustrate the correspondence of cardiac wall displacement to hemodynamic performance.

Figure 4:
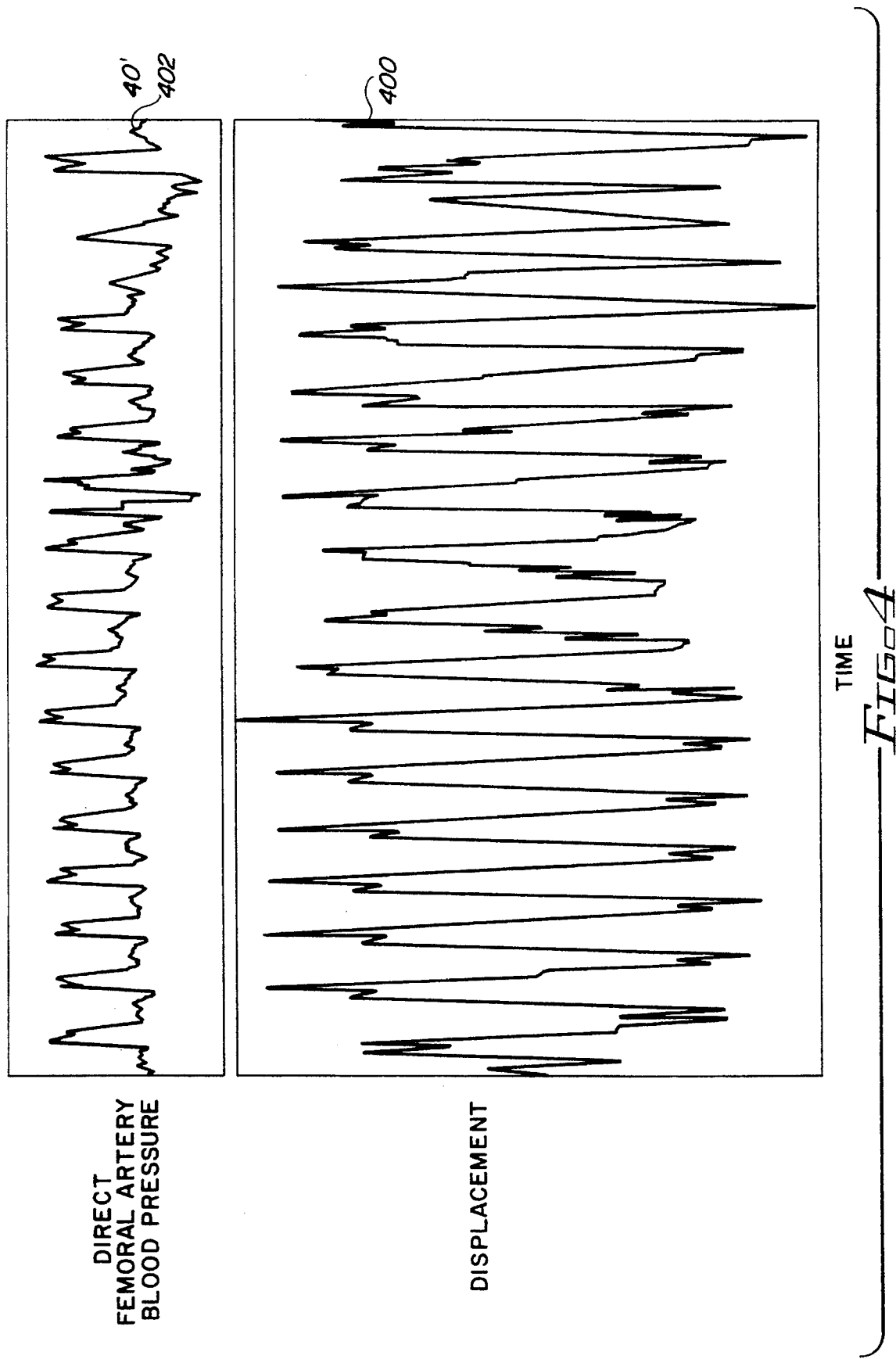
FIG. 4 is a graph showing a direct arterial blood pressure signal (the upper channel) as measured in the femoral artery and a cardiac wall displacement signal (the lower channel) derived in accordance with the principles of the present invention, both plotted simultaneously as a function of time, each indicative of a subject in normal sinus rhythm.

In FIG. 4, the cardiac wall displacement signal 400 and the arterial blood pressure signal 402 are plotted simultaneously as a function of time for a subject in normal sinus rhythm. The cardiac wall displacement signal 400 exhibits a rhythmic pattern of excursions which closely tracks the pattern of excursions corresponding to the cardiac cycle of systole (the period of contraction, or high blood pressure) and diastole (the period of filling, or low blood pressure). FIG. 4 further illustrates the one-to-one correspondence with the arterial blood pressure signal 402, that is, each excursion of the cardiac wall displacement signal 400 slightly precedes a corresponding change in arterial blood pressure, as would be expected. Each excursion in the cardiac wall displacement signal 400 is related to a volume change and corresponds to a hemodynamically effective cardiac contraction. The subject's mechanical heart rate can be determined by counting the peaks in the cardiac wall displacement signal 400 over a predetermined period of time, in a manner similar to that which may be accomplished using the arterial blood pressure signal 402. In addition, the vigor of each cardiac contraction may be determined by measuring the peak-to-peak amplitude of each excursion in the cardiac wall displacement signal 400.

Since the cardiac wall displacement signal 400 may be used to determine the subject's heart rate, it may also be used by the implantable cardiac stimulating device 300 (FIG. 3) to administer bradycardia pacing therapy, and in particular, demand pacing therapy. Demand pacing may be accomplished using the cardiac wall displacement signal 400 as follows. The microprocessor 306 (FIG. 3) receives the cardiac wall displacement signal 400 and determines the subject's heart rate by counting over a predetermined period of time, the number of excursions that have an amplitude which exceeds a threshold amplitude. The predetermined period of time and threshold amplitude may be stored as parameters in the memory 312 (FIG. 3).

If the microprocessor 306 (FIG. 3) determines that the subject's heart is beating at a physiologically acceptable rate, it inhibits the pacing pulse generator 304 (FIG. 3) from generating pacing pulses. However, once the subject's heart rate falls below an acceptable rate, the microprocessor 306 (FIG. 3) causes the pacing pulse generator 304 to generate pacing pulses which are delivered to the subject's heart through the pacing lead 302 (FIG. 3). The microprocessor 306 (FIG. 3) continues to monitor the subject's heart rate using the cardiac wall displacement signal 400 to determine when pacing pulses should be administered or inhibited.

Figure 5:
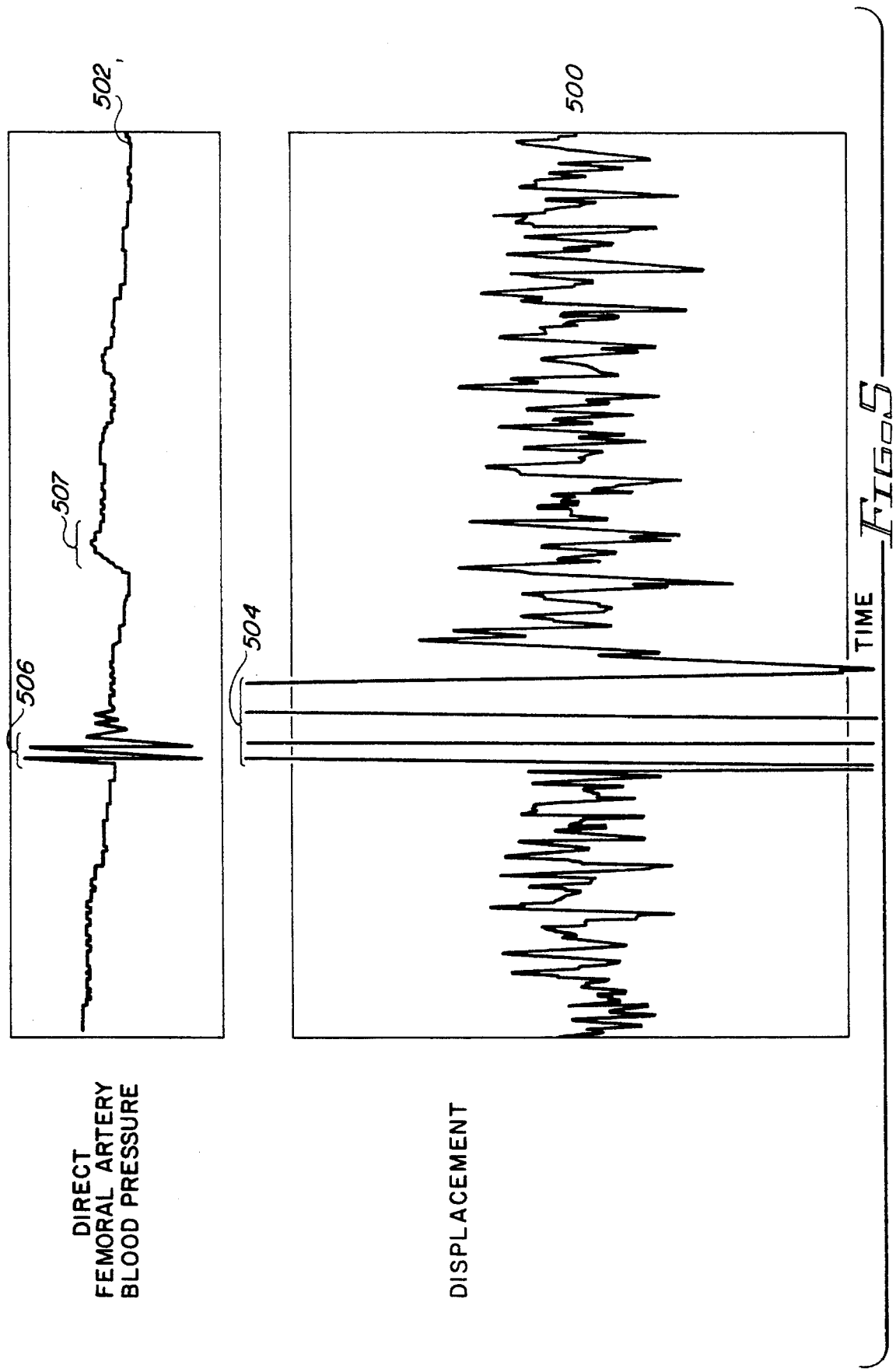
FIG. 5 is a graph showing a direct arterial blood pressure signal (the upper channel) as measured in the femoral artery and a cardiac wall displacement signal (the lower channel) derived in accordance with the principles of the present invention, both plotted simultaneously as a function of time, each indicative of a subject that first experienced fibrillation, and then hemodynamically unstable tachycardia induced by an unsuccessful defibrillation shock.

In FIG. 5, the cardiac wall displacement signal 500 and the arterial blood pressure signal 502 are plotted simultaneously as a function of time for a subject that first experienced fibrillation, and then tachycardia induced by an unsuccessful defibrillation shock. An excursion 504 in the cardiac wall displacement signal 500 represents an intense convulsion resulting from the defibrillation shock. An excursion 506 in the arterial blood pressure signal 502, signifying a rapid increase in pressure during the convulsion.

An inspection of the corresponding segments of the arterial blood pressure signal 502 reveals that arterial blood pressure dropped substantially continuously before the convulsion indicated by the excursion 506 due to fibrillation. However, arterial blood pressure increased somewhat after the convulsion (at point 507), indicating at least one effective contraction after the shock that although hemodynamic performance was compromised both before and after the convulsion, the subject's condition changed, albeit only slightly, after the defibrillation pulse was administered. More precisely, prior to the defibrillation shock, the arterial blood pressure signal 502 indicates that the subject experienced VF, and after the defibrillation shock, the subject experienced hemodynamically unstable VT. But perhaps most importantly, the cardiac wall displacement signal indicates, independently of the IEGMs, that the hemodynamic status before and after the shock is still compromised and that further and more aggressive therapy should be attempted immediately.

The segments of the cardiac wall displacement signal 500 before and after the excursion 504 exhibit rapidly appearing, low amplitude excursions when compared to the cardiac wall displacement signal 400 of FIG. 4. Thus, the cardiac wall displacement signal 500 reveals that the subject experienced hemodynamically compromising cardiac arrhythmias as effectively as the arterial blood pressure signal 502 reveals the same information. However, the excursions immediately after the shock generally have slightly higher amplitudes than the excursions in the earlier segment. Therefore, the cardiac wall displacement signal 500 not only reveals periods of hemodynamic compromise, it may also be used to detect particular types of hemodynamically compromising cardiac arrhythmias, even when the distinctions between arrhythmias are slight (i.e., VF prior to the excursion 504 and VT after the excursion 504).

Figure 6:
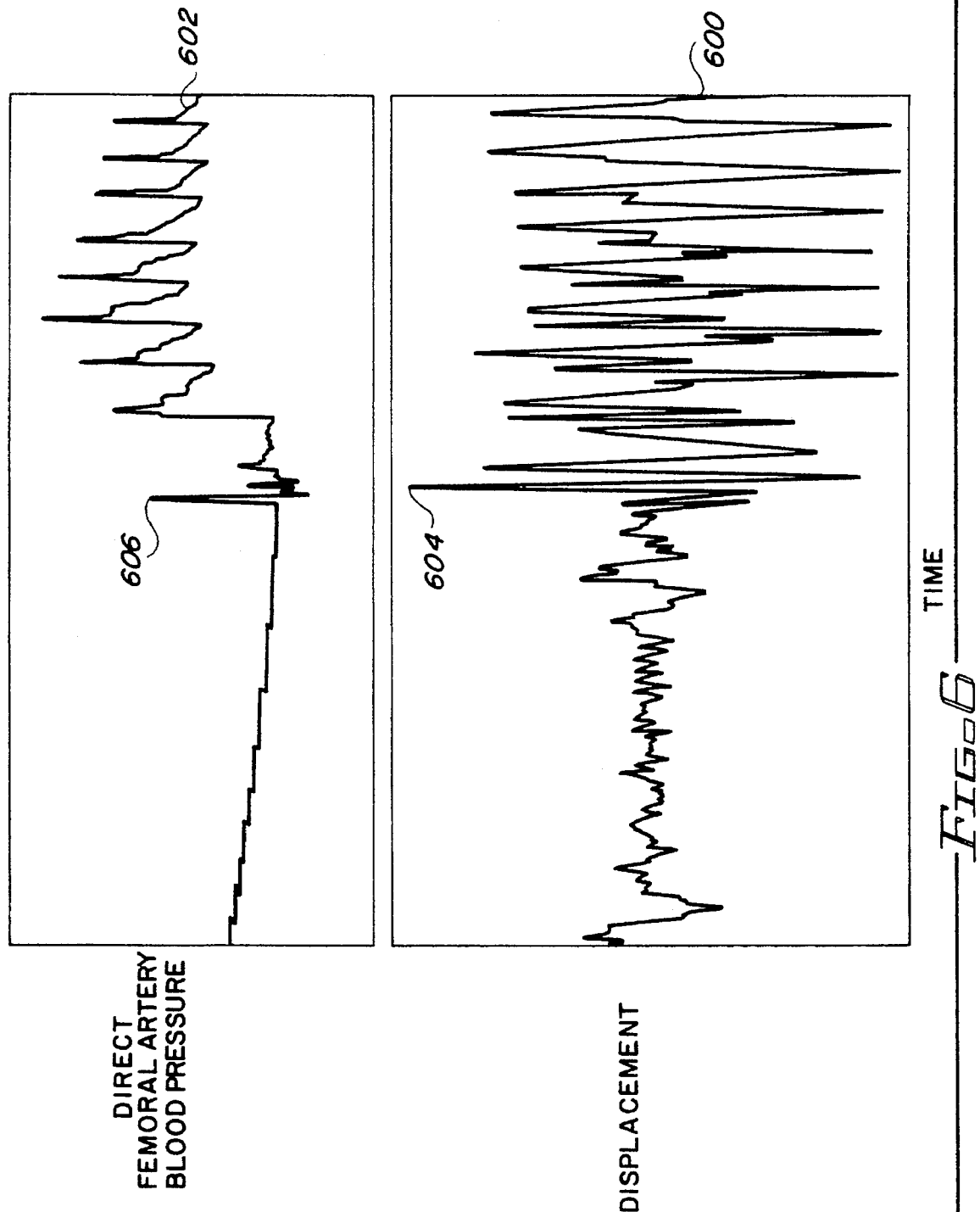
FIG. 6 is a graph showing a direct arterial blood pressure signal (the upper channel) as measured in the femoral artery and a cardiac wall displacement signal (the lower channel) derived in accordance with the principles of the present invention, both plotted simultaneously as a function of time, each indicative of a subject that experienced fibrillation and a successful defibrillation shock.

In contrast to FIG. 5, FIG. 6 shows the cardiac wall displacement signal 600 and the arterial blood pressure signal 602 from a subject that received a successful defibrillation shock. The convulsion and corresponding rise in pressure are apparent from, respectively, an excursion 604 in the cardiac wall displacement signal 600 and an excursion 606 in the arterial blood pressure signal 602. The characteristic drop in blood pressure associated with VF is evident from the segment of the arterial blood pressure signal 602 preceding the excursion 606. This hemodynamically compromising event is also apparent from the low amplitude, rapidly fluctuating segment of the cardiac wall displacement signal 600 preceding the excursion 604.

Following the defibrillation shock, the subject enters post-shock sinus rhythm, during which the subject recovers from an oxygen deficit. During this time, the arterial blood pressure signal 602 shows a rapid rise in blood pressure, followed by a gradual reduction in blood pressure as the subject recovers. Post-shock sinus rhythm is also apparent from the cardiac wall displacement signal 600, which shows large amplitude excursions appearing immediately after the excursion 604 at an extremely rapid rate. The rate gradually decreases as the subject recovers from the oxygen deficit. Therefore, the cardiac wall displacement signal indicates, independently of the IEGM, that therapy was successful and that no further therapy is needed. Both indicators are valuable in the operation of an implantable cardiovertor/defibrillator device.

When the microprocessor 306 (FIG. 3) receives an indication that the subject is experiencing one of the arrhythmias shown in FIGS. 5 and 6 (i.e., VT in the cardiac wall displacement signal 500 of FIG. 5, and VF in either of the cardiac wall displacement signals 500 and 600 of FIGS. 5 and 6, respectively), it may initiate delivery of electrical stimulation therapy to interrupt the arrhythmia. For example, if hemodynamically stable VT is indicated, the microprocessor 306 (FIG. 3) may cause the pacing pulse generator 304 (FIG. 3) to generate pacing pulses in a sequence that is known for interrupting VT. Alternatively, the microprocessor 306 (FIG. 3) may cause the high energy shock generator 308 (FIG. 3) to administer a cardioversion shock if the VT is determined to be hemodynamically unstable. If VF is indicated, the microprocessor 306 (FIG. 3) may cause the high energy shock generator 308 to administer a defibrillation shock.

FIG. 7 is presented as another illustration of the utility of cardiac wall displacement as a hemodynamic indicator. In FIG. 7, both the cardiac wall displacement signal 700 and the arterial blood pressure signal 702 reveal an ectopic heartbeat (e.g., a premature ventricular beat (PVC)) occurring during normal sinus rhythm. The ectopic heartbeat is apparent from a low amplitude excursion 704 appearing suddenly among large amplitude excursions representative of hemodynamically effective cardiac contractions in the cardiac wall displacement signal 700. A drop in blood pressure is apparent from a segment 706 of the arterial blood pressure signal 702 corresponding to the excursion 704 in the cardiac wall displacement signal 700. Although an ectopic heartbeat is not normally a hemodynamically compromising cardiac event, FIG. 7 shows that the cardiac wall displacement signal 700 provides enough resolution to detect even transient changes in hemodynamic performance. However, the reporting of ectopic beats is useful information for patients implanted with cardiac devices. For example, reporting the number of ectopic beats per hour is a useful indicator for patients undergoing serial drug testing for the suppression of such events.

Thus, a processing system for deriving cardiac wall displacement from a cardiac wall motion sensor signal and for using cardiac wall displacement as a hemodynamic indicator is provided. One skilled in the art will appreciate that the present invention can be practiced by other than the described embodiments, which are presented for purposes of illustration and not of limitation, and the present invention is limited only by the claims which follow.

What is claimed is:

1. An implantable cardiac stimulating device for providing therapeutic electrical stimulation to treat cardiac arrhythmias, the implantable cardiac stimulating device having a cardiac wall motion sensor associated therewith for providing a cardiac wall acceleration signal, the implantable cardiac stimulating device comprising:

electrical stimulation generating circuitry for generating the therapeutic electrical stimulation;

processing circuitry for deriving a hemodynamic signal representative of cardiac hemodynamic performance from the cardiac wall acceleration signal; and control circuitry for regulating the electrical stimulation generating circuitry in accordance with the hemodynamic signal.

2. The processing system of claim 1, wherein the hemodynamic signal representative of cardiac hemodynamic performance corresponds to one of contractility, sympathetic tone, blood flow, fluid displacement or stroke volume.

3. The implantable cardiac stimulating device of claim 1, wherein the processing circuitry comprises circuitry for deriving a signal representative of cardiac wall velocity from the cardiac wall acceleration signal.

4. The implantable cardiac stimulating device of claim 3, wherein the circuitry for deriving the signal representative of cardiac wall velocity comprises circuitry for integrating the cardiac wall acceleration signal over time.

5. The implantable cardiac stimulating device of claim 1, wherein the processing circuitry comprises circuitry for deriving a signal representative of cardiac wall displacement from the cardiac wall acceleration signal.

6. The implantable cardiac stimulating device of claim 5, wherein the circuitry for deriving the signal representative of cardiac wall displacement comprises circuitry for twice integrating the cardiac wall acceleration signal over time.

7. The implantable cardiac stimulating device of claim 5, wherein the processing circuitry further comprises circuitry for deriving a peak-to-peak cardiac wall displacement signal from the signal representative of cardiac wall displacement.

8. The implantable cardiac stimulating device of claim 1, wherein the processing circuitry and the control circuitry comprises a microprocessor.

9. The implantable cardiac stimulating device of claim 1, wherein the control circuitry evaluates the hemodynamic signal to detect cardiac arrhythmias and causes the electrical stimulation generating circuitry to generate the therapeutic electrical stimulation when a cardiac arrhythmia is detected.

10. The implantable cardiac stimulating device of claim 9, wherein the electrical stimulation generating circuitry comprises a pacing pulse generator for generating pacing pulses when the control circuitry detects an indication of bradycardia in the hemodynamic signal.

11. The implantable cardiac stimulating device of claim 9, wherein the electrical stimulation generating circuitry comprises a pacing pulse generator for generating pacing pulses in a sequence for interrupting tachycardia when the control circuitry detects an indication of hemodynamically stable tachycardia in the hemodynamic signal.

12. The implantable cardiac stimulating device of claim 9, wherein the electrical stimulation generating circuitry comprises a high energy shock generator for generating a cardioversion shock when the control circuitry detects an indication of hemodynamically unstable tachycardia in the hemodynamic signal.

13. The implantable cardiac stimulating device of claim 9, wherein the electrical stimulation generating circuitry comprises a high energy shock generator for generating a defibrillation shock when the control circuitry detects an indication of fibrillation in the hemodynamic signal.

14. The implantable cardiac stimulating device of claim 1, further comprising:

means for sensing cardiac depolarization signals;

means for detecting a decrease in the hemodynamic signal;

means for defining a cardiac depolarization signal as an ectopic beat whenever a corresponding decrease in the hemodynamic signal is detected; and means for storing information related to the detected ectopic beats.

15. A method of providing therapeutic electrical stimulation to treat cardiac arrhythmias, comprising the steps of:

receiving a cardiac wall acceleration signal from a cardiac wall motion sensor;

deriving a hemodynamic signal representative of cardiac hemodynamic performance from the cardiac wall acceleration signal; and regulating delivery of the therapeutic electrical stimulation in accordance with the hemodynamic signal.

16. The method of claim 15, further comprising the steps of:

sensing cardiac depolarization signals;

detecting a decrease in the hemodynamic signal;

defining a cardiac depolarization signal as an ectopic beat whenever a corresponding decrease in the hemodynamic signal is detected; and storing information related to the detected ectopic beats in memory.

17. The method of claim 15, wherein the step of deriving a hemodynamic signal comprises the step of deriving a signal representative of cardiac wall velocity from the cardiac wall acceleration signal.

18. The method of claim 17, wherein the step of deriving the signal representative of cardiac wall velocity comprises the step of integrating the cardiac wall acceleration signal over time.

19. The method of claim 15, wherein the step of deriving a hemodynamic signal comprises the step of deriving a signal representative of cardiac wall displacement from the cardiac wall acceleration signal.

20. The method of claim 19, wherein the step of deriving the signal representative of cardiac wall displacement comprises the step of twice integrating the cardiac wall acceleration signal over time.

21. The method of claim 19, wherein the step of deriving a hemodynamic signal further comprises the step of deriving a peak-to-peak cardiac wall displacement signal from the signal representative of cardiac wall displacement.

22. The method of claim 19, wherein the regulating step comprises the steps of:

evaluating the hemodynamic signal to detect cardiac arrhythmias; and causing delivery of the therapeutic electrical stimulation when a cardiac arrhythmia is detected.

23. The method of claim 22, wherein the step of causing delivery of the therapeutic electrical stimulation comprises the step of causing delivery of pacing pulses when the hemodynamic signal is indicative of bradycardia.

24. The method of claim 22, wherein the step of causing delivery of the therapeutic electrical stimulation comprises the step of causing delivery of pacing pulses in a sequence for interrupting tachycardia when the hemodynamic signal is indicative of hemodynamically stable tachycardia.

25. The method of claim 22, wherein the step of causing delivery of the therapeutic electrical stimulation comprises the step of causing delivery of a cardioversion shock when the hemodynamic signal is indicative of hemodynamically unstable tachycardia.

26. The method of claim 22, wherein the step of causing delivery of the therapeutic electrical stimulation comprises the step of causing delivery of a defibrillation shock when the hemodynamic signal is indicative of fibrillation.

\* \* \* \* \*